United States Patent [19]

Chang et al.

[11] Patent Number: 4,731,649
[45] Date of Patent: Mar. 15, 1988

[54] OBLIQUE ILLUMINATION FOR VIDEO RIM INSPECTION

[75] Inventors: Roger Chang, Ft. Lauderdale; Donald Darling, Palm Beach Gardens; Dale Kline, Palm Beach, all of Fla.

[73] Assignee: Vistech Corp., West Palm Beach, Fla.

[21] Appl. No.: 906,297

[22] Filed: Sep. 11, 1986

[51] Int. Cl.⁴ .............................................. H04N 7/18
[52] U.S. Cl. ................................ 358/106; 250/223 B; 356/240; 356/428
[58] Field of Search ....................... 358/101, 106, 107; 209/526; 250/223 B; 356/240, 428; 362/308, 311

[56] References Cited

U.S. PATENT DOCUMENTS

| 3,386,579 | 6/1968 | Schulge et al. | 250/224 |
| 3,631,255 | 12/1971 | Gender | 250/223 B |
| 4,002,823 | 1/1977 | Van Oosterhout | 358/106 |
| 4,026,414 | 5/1977 | Ellinger | 250/223 B |
| 4,208,130 | 6/1980 | Saconney et al. | 356/428 |
| 4,213,042 | 7/1980 | Beach et al. | 250/223 B |
| 4,391,373 | 7/1983 | Wiggins | 250/223 B |
| 4,454,542 | 6/1984 | Miyazawa | 358/106 |
| 4,460,940 | 7/1984 | Mori | 362/311 |
| 4,606,635 | 8/1986 | Miyazawa et al. | 356/240 |

Primary Examiner—Howard W. Britton
Assistant Examiner—John K. Peng
Attorney, Agent, or Firm—Steele, Gould & Fried

[57] ABSTRACT

An illumination system for video inspection of transparent and translucent bodies to be inspected sequentially while moving along a conveying path has a light source and light-transmitting block partly enclosing over the end of the bodies moving on the path. A light source, especially one or more strobe lamps is located along the conveying path, and light from the source is directed inwardly by the block to a diffuse surface defining side walls of a channel through which rims move along the conveying path. The diffuse side walls direct light inwardly and obliquely of the rim. The rim can be illuminated on the fore and aft sides in the channel by light emission from an additional block of material forming a connection web between the inwardly-reflective blocks, tending to evenly illuminate the rim.

9 Claims, 6 Drawing Figures

OBLIQUE ILLUMINATION FOR VIDEO RIM INSPECTION

BACKGROUND OF THE INVENTION

1. Field of the Invention

This invention relates to the field of video inspection systems for container rims, and more particularly to an illumination device for bottle sealing rims, the device directing light inwardly and obliquely of the rim for developing a video image with minimum brightness variation apart from variations due to defects in the rim.

2. Prior Art

The prior art includes the use of techniques relying on light scattering by rim defects for discriminating between good rims and bad rims in containers such as soft drink bottles and the like. A video scanning system in which digitized data representing pixel brightness is compared for adjacent pixels to discriminate defects is disclosed, for example, in U.S. Pat. No. 4,454,542—Miyazawa, the video data processing aspects of which are incorporated herein by reference. Brightness comparison techniques rely on even illumination of the article being inspected, because uneven illumination may cause brightness variations, reflections and the like that are not easily distinguished from defects. The Miyazawa system is effective from an image-analysis standpoint, but teaches illuminating the container and its rim by light from an annular source above the container. The light is directed substantially along the axis of the container, which is generally-cylindrical.

Axially illuminating a container can be arranged by directing light through a transparent base while viewing axially toward the rim, or by means of an annular diffuse light source through which annular source the rim is viewed from above. In the event the containers are to be movable relative to the inspection system without undue mechanical complexity, at right angles to the container axis, such an annular source is necessarily positioned at a space above the rim, and accordingly cannot provide a diffuse illumination of the rim from the sides of the conveying path, in particular including obliquely-directed light rays passing through the rim upwardly and inwardly with respect to the axis of view. On the other hand, only an annular shape is symmetrical and will evenly illuminate the rim around its circumference.

A typical bottle rim for a soft drink or the like has a rounded annular or toroidal sealing surface defining a shape that can sealably receive a cap and can be placed against a customer's lips. For some bottles the rim is threaded, for others merely rounded. Almost any defect in a rim is grounds to reject the container. However, defects that occur in threads or around the lower part of the toroidal sealing surface are not readily visible in a view along the bottle axis, and may even be concealed by too much reliance on axially-oriented illumination. Rim inspection systems therefore are characterized either by asymmetrical illumination or illumination that is not directed obliquely upward to disclose defects present in the area of a lower edge of the sealing surface.

U.S. Pat. No. 3,631,255—Gender, et al has means reaching over the rim. The patent teaches a rim inspection system in which light is to be directed inwardly along a conveying path defining an arc by means of a plurality of point sources spaced evenly along the conveying path. This patent teaches illuminating the rim using substantially-radially directed light. Any defect such as a sealing ring chip or irregularity causes additional light to be directed upwardly along the axis of the container due to scattering of light beams. The light level is detected by a photo multiplier detector and presumably compared to a rejection threshold. The patent requires developing a sharp variation in the level of axially-directed light between a good rim in which radial light rays pass radially through the rim and a bad rim in which the radially-directed rays are re-directed along the axis of the container to the detector. This average light level technique is somewhat different than a video inspection system in which results are best if the rim is evenly illuminated and the brightness level of adjacent pixels is compared. The average level technique does not require even illumination as does the video technique.

U.S Pat. Nos. 4,391,373—Wiggins and 4,213,042—Beach, et al, also teach devices having channel-like housings extending over the rim. These patents both concern paired light sources and photocells. Although the optical paths between these paired elements are inclined obliquely to the axis of the bottle, the disclosure does not suggest how such an arrangement might be adapted to a video analysis technique in which diffuse, even illumination is needed. Their disclosures are much like Gender's threshold comparison, but use discrete optical paths.

U.S. Pat. Nos. 4,208,130—Saconney, et al and 3,386,579—Schulze teach devices in which an effort is made to illuminate a rim such that light is directed at a plurality of angles toward or away from the rim. These patents show a means for expanding the photocell pair or plural light source ideas of the prior art in a way that more evenly illuminates the rim, but these patents, together with those mentioned above are characterized by a plurality of discrete sources that would produce light variations of themselves, apart from defects. The patents lack an illumination element in which a bottle rim is evenly diffusely illuminated for video analysis, including oblique upward illumination, but allowing the bottles to move relative to the inspection device without interruption.

According to the invention, a diffuse light-source element defined by a number of strobe lamps or the like and a monolithic, internally-reflective prism device having diffuse side walls directing light radially inwardly and obliquely upward adjacent the rim, is provided together with a pixel-comparison video analysis system viewing the container along its axis, the video view being taken through an opening in the monolithic illumination element. The diffuse illumination over a wide area provides a very even illumination for the bottle. Masking of certain parts of the opening through which the video detector views allows the element to provide some illumination even toward the sides directed fore and aft along the conveying path. Preferably, the illumination element and its prism parts are substantially longer in the conveying direction than the bottle, thereby minimizing directional effects, and illuminating the rim substantially evenly around its circumference and from oblique aspects above and below.

Reflective prism elements according to the invention are trapezoidal in section, having an outer internally-reflective wall disposed at about 45° to bottle axis and to the light source, directing light rays inwardly toward the rim. A diffuse surface adjacent the rim defines a wall of a channel enclosing over the rim oriented substantially parallel to the bottle axis. The diffuse surface receives light internally reflected from the source and internally reflective prism, illuminating the rim in the area of the viewing port. Preferably, two such prism elements are provided on opposite sides of the conveying path, and are affixed via a light transmissive panel having the viewing port therein, and to which the light sources, preferably strobe flash tubes operable to "freeze" the image in place, are attached. In this manner, high levels of illumination are provided and the illumination is quite even and includes oblique rays. The illumination is adequate for high resolution comparisons of pixel brightness, facilitating discrimination of rim defects without the need to stop the bottles in their movement along the conveying path.

SUMMARY OF THE INVENTION

It is an object of the invention to evenly illuminate the rims of transparent or translucent containers moving continuously along a conveying path, for purposes of video analysis of pixel brightness to detect defects in the rims.

It is another object of the invention to evenly illuminate rims of bottles on a conveyor using a convenient illumination means in which light sources are conveniently mounted remote from the area of effective light emission.

It is a further object of the invention to provide a rim illumination device that is effective and compact, and can be readily incorporated into an overall container inspection system.

It is still another object of the invention to provide a rim inspection illumination means that is durable and inexpensively constructed.

These and other objects are accomplished by an illumination system for video inspection of transparent and translucent bodies to be inspected sequentially while moving along a conveying path. The system has at least one light source directed into a prism-like light-transmitting block that partly encloses over the rim end of the bodies moving on the path. The light sources, especially linear strobe lamps are preferably placed parallel to the conveying path, and light from the sources is directed inwardly by the block to a diffuse light emitting surface defining elongated side walls along the conveying path. The diffuse side walls direct light inwardly and obliquely with respect to an axis of the rim. The rim is further illuminated on the fore and aft sides in the conveying direction from an additional block of light transmitting material forming a connection web between the inwardly-reflective prism parts of the light transmissive block.

BRIEF DESCRIPTION OF THE DRAWINGS

There are shown in the drawings the embodiments that are presently preferred. It should be understood that the invention is not limited to the precise arrangement and instrumentalities shown in the drawings, wherein.

DETAILED DESCRIPTION OF THE PREFERRED EMBODIMENTS

Figure 1:
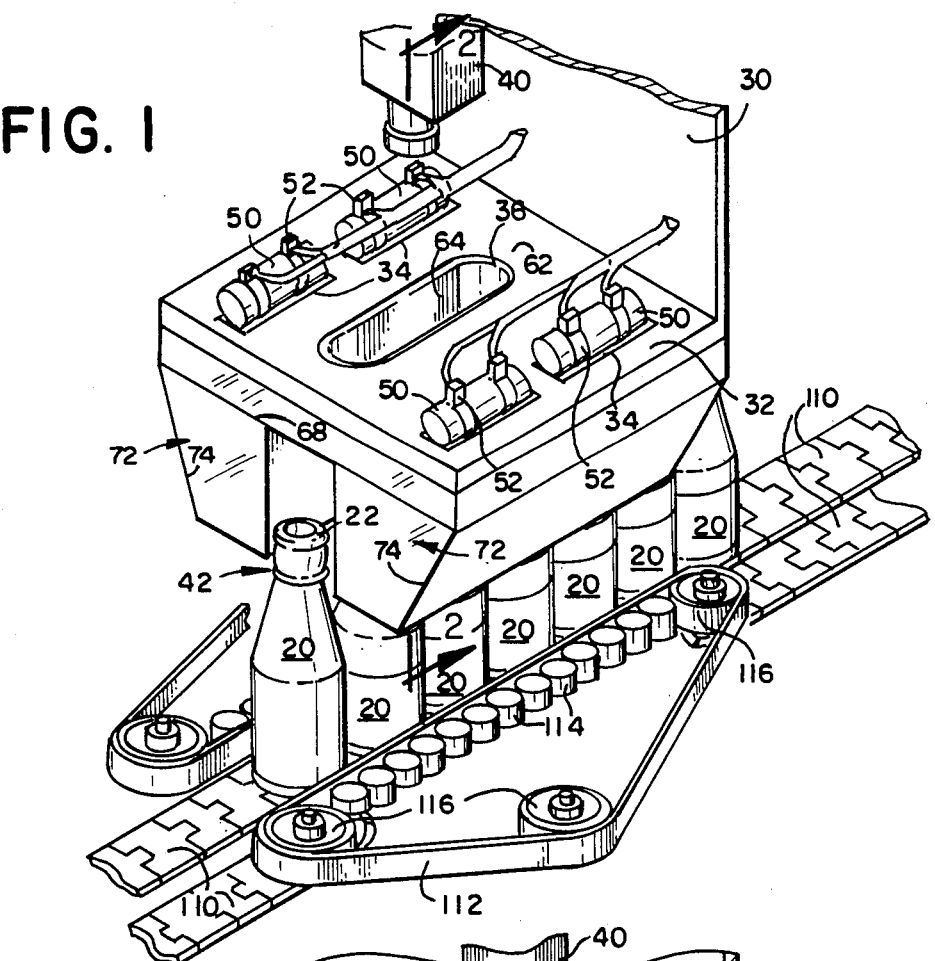
FIG. 1 is a perspective view showing operative parts of the rim inspection and illumination means according to the invention.
Figure 4:
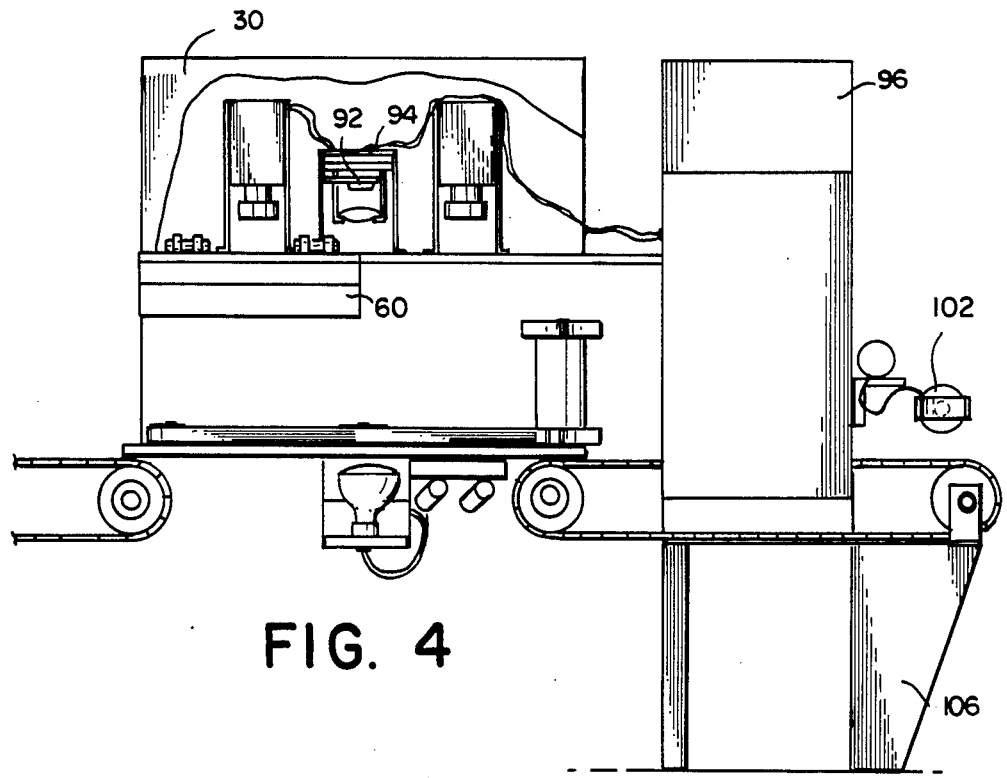
FIG. 4 is an assembly view showing the inspection and illumination system incorporated in an overall bottle inspection device.

FIG. 1 shows a perspective view of a preferred embodiment of the rim inspection system with housing portions cut away to reveal the operative parts. In general, containers 20 are positioned immediately after one another and are moving along a conveyor that carries the containers from underneath. The conveyor may include one or more endless belt sections 110, may be continuous through a rim inspection zone according to the invention, or may interrupted as shown in FIG. 1 by a section driven via side-engaging transport belt 112. In FIG. 1, belt 112 transports the bottles across a gap between spaced endless conveyor sections 110, by means of drive and idler pulleys 116 and transport rollers 114, the bottles 20 being carried between belts 112 frictionally holding the bottles (or other containers) on both sides of the conveyor. The rim illumination appartus according to the invention does not require a bridging transport belt 112; however, the rim inspection device is preferably included with other inspection devices as shown in FIG. 4, including for example a bottom inspection device that requires unobstructed view of the bottom of the bottle or other container. Accordingly, a gap is provided in which the links of the endless belts 110 are omitted for access to the bottoms of containers.

A rim inspection video camera 40 is positioned in a housing 30 above the bottles 20, and directed downwardly to record a plan view of each rim 22 passing by. A light source/photocell pair having a beam crossing the conveying path can be employed in connection with video camera 40 to record a frame when a bottle 20 is precisely in position under camera 40. The photocell triggering signal operates the strobe and the camera such that strobe lights 50 are triggered and a frame is captured by video camera 40 when each successive bottle 20 is in precisely the correct position. However, it is also possible to trigger the strobe lamps 50 immediately before the next video frame synch for a free running video camera 40, thereby capturing the rim image at an indefinite position in the frame, or otherwise to synchronize to the rim position for purposes of analysis.

The bottom wall 32 of housing 30 has means for mounting each of the strobe lamps 50 or other light bulbs, for example including spring clip connectors 52 that position strobe lamps 50 directly over openings 34 in bottom wall 32, allowing light from strobes 50 to be directed downward. By means of internal reflections and surface diffuseness in block 60, which has prismatic surfaces directing light from strobes 50 to a diffuse illuminating surface, the rim 22 is evenly illuminated from above and below the cap-sealing edges of the rim 22.

Successive rims 22 move through a channel 42 aligned parallel to the conveying path and defined between inward facing walls 76 of blocks 60. Blocks 60 are preferably clear plastic, e.g., polycarbonate (such as "Plexiglass"). Walls 76 are adapted for diffuse light transmission, being, for example, roughened by coarse cutting, sanding or the like. Light striking surfaces 76 from inside causes the block to emit an even glow, that will illuminate rim 22 without producing any particularly light or dark areas of illumination. With very even lighting, the video analysis can include a close examination of small variations in light and dark levels across the image recorded. Defects, for example the chip 24 shown in FIGS. 2 and 3, produce sharply-defined lines of contrast across which the brightness varies substantially. Under simple illumination, a similar variation in brightness may occur adjacent a reflection of a bulb or similar light source in the shiny glass rim. Accordingly, the invention avoids any reflections by illumination using a diffuse surface, and by spreading the diffuse surface over a range of incident angles to the rim, including above, below and fore and aft of the conveying direction.

Lens block 60 is preferably a composite produced by a pair of prism blocks 72, each having an inclined outer surface 74 polished or covered with a light-colored or even mirror-like material, thereby directing light inwardly toward the conveying path. These prism blocks 72 are rigidly affixed to a mounting panel block 62 that is also light transmissive and, together with the prisms, defines the channel through which the rims of conveyed bottles move. Panel 62 defines the web of the channel and prism blocks 72 define the opposite walls. Blocks 72 and panel 62 are joined across a junction 68 that permits the passage of light from strobe light sources 50, downwardly into prism 72.

Preferably, reflective surfaces 74 are inclined at about 45 degrees and strobe sources 50 are substantially centered over reflective surfaces 74, to thereby direct the greater part of the strobe illumination perpendicularly toward diffuse surfaces 76.

Figure 2:
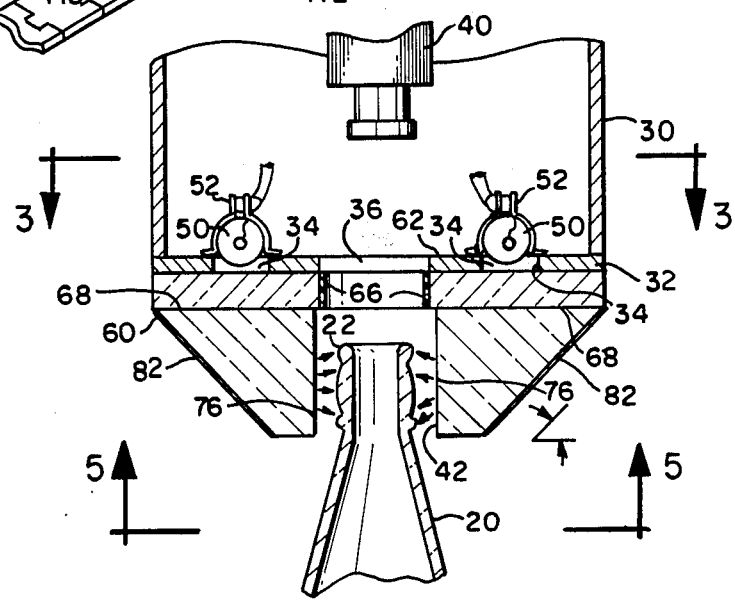
FIG. 2 is a partial section view taken along lines 2—2 in FIG. 1.

FIG. 2 shows a partial section view of the apparatus, viewing along the conveying path. As shown in FIG. 2, windows 34 (i.e., openings in member 32 of housing 30) are disposed under strobe lamps 50 and allow light to pass downwardly through panel 62, across junction 68 and into prism block 72. FIG. 2 illustrates an embodiment in which the angled reflective surfaces, which need 74 not be polished, are provided with diffuse reflective means 82, for example a white, diffuse tape on the adhesive side, thereby reflecting light generally inwardly toward diffuse transmissive surfaces 76 defining channel 42.

Other possibilities exist for directing light inwardly to be diffusely emitted adjacent the rim and there caused to direct light inwardly and upwardly. Rather than using reflective tape or the like to reflect light from diffuse reflective means 82 inwardly, it is also possible for example, to paint surfaces 74 white, to abrade them, etc.

Figure 2A:
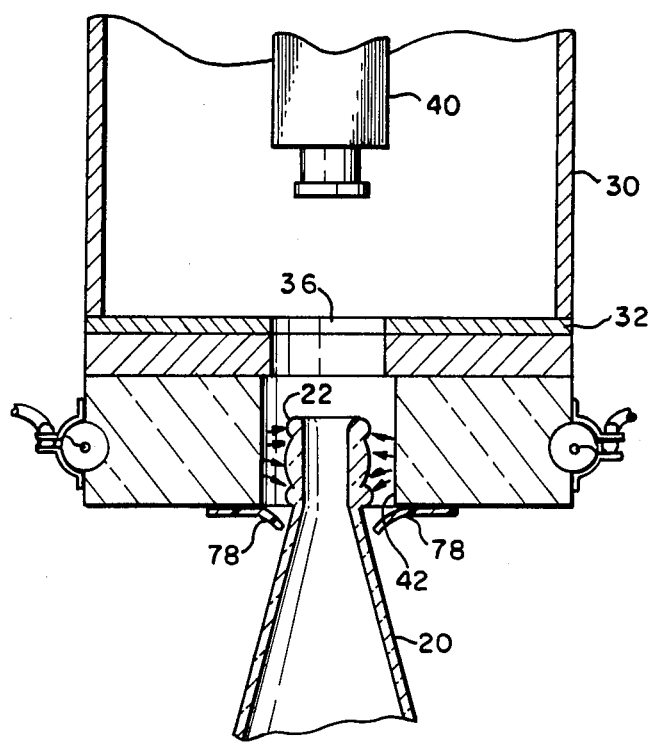
FIG. 2a is a corresponding partial section view for an alternative embodiment.

In an alternative embodiment of the invention, strobe lamps 50 can be mounted at the outer surfaces 74 of the block rather than above the block. Such an embodiment is shown in FIG. 2a. In this event the outer surfaces of the block can simply be vertical or can define a groove in which the lamps 50 are received along the outer edges. In any event, the light from the lamps 50 is directed toward diffuse surfaces 76, defining a part of the channel encompassing the rim. In each of the embodiments, a diffuse illuminated surface extending along sides of the rim causes inwardly and upwardly directed light to clearly show rim defects for axial viewing from above.

Figure 3:
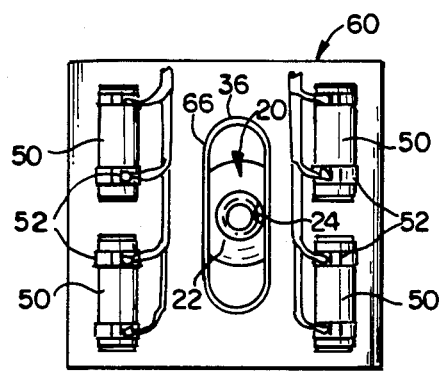
FIG. 3 is a plan view along lines 3—3 in FIG. 2.

Channel 42 and its diffuse surfaces 76 are elongated along the conveying path, and thereby provide illumination that is substantially even around the whole circumference of rim 22. However, inasmuch as surfaces 76 are located on the sides of the channel and not in the fore and aft directions relative to the rim, it is preferred to supplement the light applied to the fore and aft sides of rim 22, by supplemental light emission from panel 62 defining the web of the channel. As shown in FIG. 3, the opening 36 through which the rim 22 is viewed by the video camera is an elongated oval in the direction of conveying. Opaque tape 66 is applied to cover the inward facing upper portion of opening 36, along the sides corresponding to side wall 76. The fore and aft ends of opening 36, however, are not blocked by tape 66 and therefore emit light. Opening 36 being elongated, the light emission from panel 62 is spaced somewhat farther from rim 22 than the emission from diffuse side wall 76. The inner portion of opening 36 is preferably also roughened at the ends to provide a diffuse emission of light on the ends fore and aft along the oval hole. The light emission from panel 62 and prisms 72 together provide a diffuse illumination all around rim 22.

The preferred oval viewing opening shown allows rim viewing anywhere along the longer axis of the oval. It is also possible to use a circular or other shape of viewing opening, and/or to modify the light shielding of masking 64 as required. In the alternative embodiment of FIG. 2a, the viewing opening 36 is round and not masked, and a pair of light shields 78 extend inwardly from the bottom of blocks 72 to avoid illuminating bottle features lower than the rim, such as labels. It will be appreciated that some tradeoffs such as these may detract from even illumination but may be justified to reduce costs and complexity.

FIG. 3 illustrates the spring clips 52 by means of which strobe bulbs 50 can be affixed over openings 34 in the bottom wall 32 of housing 30. The spring clips 52 can function as electrical connectors, or electrical connection can be made otherwise. Acceptable strobe lamps are available in various shapes and sizes. In lieu of the paired lamps shown, alternatives include elongated lamps one on each side, a U-shaped lamp with legs of the U on each side (perhaps with the connecting part masked), etc. It is presently preferred that the strobe lights 50 be high voltage apparatus (e.g., about 600 volts pulsed), thereby presenting a certain shock hazard. The duration of the strobe should be sufficiently short to effectively "freeze" bottles 20 in position on the conveyor. The strobe must be long enough in duration, however, to produce an image in the video detector 40. Preferably, detector 40 is a charge coupled device in which pixels in an X-Y planar array are addressable to read out an analog signal relating to illumination intensity. The analog outputs for each pixel can be read out to form a video signal which can be sampled and digitized to define pixels in a second array, of n-m pixels where n and m are not necessarily equal to X and Y. The detector is further provided with control and addressing means and an A to D converter to produce a pixel array in digitally encoded grey levels to a resolution allowing comparison for purposes of contrast. A means for analyzing data in a CCD camera is disclosed in U.S. Pat. No. 4,454,542—Miyazawa, to which reference is made above.

Channel 42, bounded by diffuse wall 76 on either side of the conveying path and supplementally illuminated through diffuse end portions of opening 36 in the fore and aft directions, is preferably substantially longer than the rim under inspection. The rim may be, for example, 3 cm in diameter. The diffuse light path defined by walls 76, however, should be on the order of 15 cm, whereby notwithstanding the lack of side wall illumination in the fore and aft directions corresponding directly to diffuse walls 76, the rims are adequately illuminated at approximately the same levels as the side walls due to the relatively long channel length compared to rim diameter.

Figure 5:
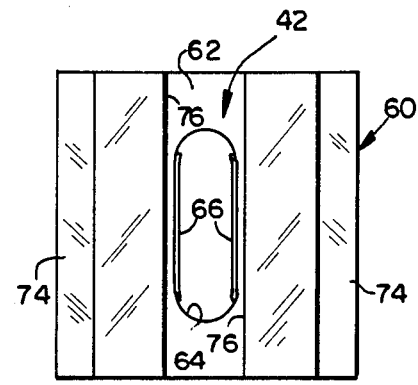
FIG. 5 is an elevation view taken along lines 5—5 in FIG. 2.

FIG. 5 shows a bottom view of the lens block. Channel 42 is shown bounded by diffuse walls 76 on either side. The web portion of the channel defined by panel 62 has opening 64, to which opaque tape 66 is applied along the sides but not the diffuse ends through which supplemental light passes. Accordingly, light reflected by inclined wall 74 and thereafter emitted by diffuse wall 76, as supplemented by the light emitted from the unmasked ends of opening 64, in the fore and aft directions, evenly illuminates the rim.

The device of the invention is preferably employed as an axial inspection element in an overall bottle inspection system as shown in FIG. 4. Camera 40, viewing the rims of bottles through lens block 60, may be positioned adjacent a bottom inspection camera 94 and 92 for monitoring the absorption of energy by the container as a means for detecting residual water. Detector 92 may be sensitive, for example, to changes in capacitance, infrared absorption or the like. The bottom inspection camera 94 is downwardly oriented over a transparent panel with additional light sources (e.g., strobe lamps) being placed under the transparent panel. Inasmuch as detector 92 and bottom inspection system 94 require an unobstructed view of the bottom of the container, these items may be employed together with detector 40 over a gap in the conveyor in which bottom supporting conveyor link sections 110 are bridged by a belt 112 transporting the containers from the sides. These inspection elements can be also used together with a side wall inspection device 96, which is not shown herein in detail. Any defects detected by any of the inspection apparatus can be timed together with reject kicker 102 to urge rejected containers off the conveyor and, for example, into a reject chute 106.

The invention having been disclosed, additional variations will now occur to persons skilled in the art. Reference should be made to the appended claims rather than the foregoing specification as indicating the true scope of the invention.

What is claimed is:

1. An inspection system for examining an end of transparent and translucent bodies, each of the bodies to be inspected while progressing along a conveying path, the system comprising:

a video analyzer directed axially toward the end and being operable to record an instantaneous image of the end and to discriminate between good and bad ends by detecting effects therein;

at least one light source for illuminating the end; and, a block of light-transmitting material illuminated by the light source, the block defining sidewalls reaching over the end of the body to partly surround the end of the body as the body is moved along the conveying path, the block having a diffuse, light-transmissive surface, and light being directed inwardly from the block toward the end and obliquely toward said end and toward the video analyzer.

2. The inspection system of claim 1, wherein the light source has light-emitting portions disposed against the block on opposite sides of the path.

3. The inspection system of claim 2, wherein the light source includes strobe lamps mounted on an opposite side of the block from the body.

4. The inspection system of claim 3, wherein the block is shaped as a channel enclosing over a path followed by the end as the body moves along the conveying path, the block having an opening in a central web of the channel, the video analyzer being directed toward the opening.

5. The inspection system of claim 4, wherein the block has oblique outer walls forming internally-reflective surfaces directing light inwardly to the diffuse surface of the side walls.

6. The inspection system of claim 5, wherein the block is a composite of substantially-transparent material including a panel disposed over the conveying path and two prisms, the prisms having internally-reflective surfaces on outer sides directed away from the conveying path, said internally reflective surfaces reflecting light inwardly toward the diffuse surfaces of the side walls, the light-emitting portions being disposed in a linear array along the conveying path.

7. The inspection system of claim 6, wherein the opening in the central web has an opaque covering along parts of the opening coextensive with the side walls, and the central web has light transmissive surfaces at leading and trailing edges along the conveying path, whereby light transmitted through the central web illuminates said end on leading and trailing parts with respect to the conveying path.

8. The inspection system of claim 1, wherein the block is formed of a polycarbonate panel and two polycarbonate prisms, the panel and prisms being affixed to one another and the prisms having outer walls disposed at about 45° to the panel and the side walls being substantially perpendicular to the panel.

9. The inspection system of claim 1, wherein the video analyzer includes digital means for recording pixel brightness data at a plurality of points in an image including a top view of the end of the body, illuminated by light directed inwardly from the block of light transmitting material along lines oriented inwardly toward the end and obliquely of the end.

* * * * *